(12) United States Patent
Winokur

(10) Patent No.: US 6,245,797 B1
(45) Date of Patent: Jun. 12, 2001

(54) COMBINATION THERAPY FOR REDUCING THE RISKS ASSOCIATED WITH CARDIO- AND-CEREBROVASCULAR DISEASE

(75) Inventor: Melvin Winokur, Cedar Grove, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/179,349

(22) Filed: Oct. 20, 1998

Related U.S. Application Data

(60) Provisional application No. 60/062,691, filed on Oct. 22, 1997.

(51) Int. Cl.$^7$ .................. A01N 43/56; A61K 31/415
(52) U.S. Cl. ............... 514/406; 514/252.06; 514/386; 514/415; 514/437; 514/438; 514/461
(58) Field of Search .................. 514/252.06, 386, 514/406, 474, 415, 437, 438, 461

(56) References Cited

FOREIGN PATENT DOCUMENTS

WO 97/21445  6/1997  (WO).
WO 98/50033  11/1998  (WO).

OTHER PUBLICATIONS

Pallenberg, et al. Database Hcaplus on Stn. an 1997:121345, 1996.
P. M. Ridker, et al., "Inflammation, Aspirin, and the Risk of Cardiovascular Disease in Apparently Healthy Men", The New England Journal of Medicine, vol. 336, No. 14, pp. 973–979, Apr. 3, 1997.

Primary Examiner—Dwayne C. Jones
(74) Attorney, Agent, or Firm—Carol S. Quagliato; Richard C. Billups

(57) ABSTRACT

The instant invention provides a drug combination comprised of an HMG-CoA reductase inhibitor in combination with a COX-2 inhibitor, which is useful for treating, preventing, and/or reducing the risk of developing atherosclerosis and atherosclerotic disease events.

54 Claims, No Drawings

COMBINATION THERAPY FOR REDUCING THE RISKS ASSOCIATED WITH CARDIO- AND-CEREBROVASCULAR DISEASE

CROSS REFERENCE TO RELATED APPLICATIONS

This application is a non-provisional application related to U.S. application Ser. No. 60/062,691 filed on Oct. 22, 1997 priority of which is claimed hereunder.

FIELD OF THE INVENTION

The instant invention involves a drug combination comprising a 3-hydroxy-3-methylglutaryl coenzyme A (HMG-CoA) reductase inhibitor (or HMG-CoA RI) in combination with an inhibitor of cyclooxygenase-2.

BACKGROUND OF THE INVENTION

Inhibitors of cyclooxygenase-2 are a sub-class of the class of drugs known as non-steroidal antiinflammatory drugs (NSAIDs). The NSAIDs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandin by inhibiting enzymes in the human arachidonic acid/prostaglandin pathway including the enzyme cyclooxygenase (COX). The recent discovery that there are two isoforms of the COX enzyme, the first, COX-1, being involved with physiological functions and the second, COX-2, being induced in inflamed tissue, has given rise to a new approach. While conventional NSAIDs block both forms of the enzyme, the identification of the inducible COX-2 enzyme associated with inflammation has provided a viable target of inhibition which more effectively reduces inflammation and produces fewer and less drastic side effects. Many compounds which have activity as COX-2 inhibitors have been identified, and much research continues in this area.

Recently, a study published in N. Eng. J. Med. (Apr. 3, 1997) found that after several years of low-level inflammation, men are three times as likely to suffer heart attacks and twice as likely to have strokes. The study evaluated 1,086 men with levels of the C-reactive protein considered to be within normal range. Researchers found that those whose levels were in the upper 25% of the group were three times more likely to have suffered a heart attack more than six years later, and twice as likely to have a stroke than those whose levels were in the lowest 25%. Aspirin's benefits were particularly pronounced in the group with highest levels of the protein, suggesting that its anti-inflammatory effects were responsible for reduction in heart attacks and strokes.

It has been clear for several decades that elevated blood cholesterol is a major risk factor for coronary heart disease, and many studies have shown that the risk of coronary heart disease (CHD) events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDIL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events.

Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

Improved therapies for treating, preventing and reducing the risk of developing atherosclerosis, and cardiovascular and cerebrovascular events and related disorders are currently being sought for the large number of individuals who are at risk for these disorders. The instant invention addresses this problem by providing a combination therapy comprised of an HMG-CoA RI with a COX-2 inhibitor. When administered as part of a combination therapy, the COX-2 inhibitor together with the HMG-CoA RI provide enhanced treatment options as compared to administration of either the HMG-CoA RI or the COX-2 inhibitor alone.

SUMMARY OF THE INVENTION

The instant invention provides a novel drug combination comprised of an HMG-CoA reductase inhibitor in combination with a COX-2 inhibitor, which is useful for treating, preventing, and/or reducing the risk of developing atherosclerosis and atherosclerotic disease events.

One object of the instant invention is to administer the above-described combination therapy to people who do not yet show clinical signs of atherosclerosis, but who are at risk of developing atherosclerosis and associated diseases. Clinical manifestations of atherosclerosis include atherosclerotic cardiovascular disease such as coronary heart disease (also known as ischemic heart disease), cerebrovascular disease, and peripheral vessel disease. Toward this end, the instant invention provides methods for preventing or reducing the risk of developing atherosclerotic cardiovascular disease, coronary heart disease, cerebrovascular disease and peripheral vessel disease, and preventing or reducing the risk of a first or subsequent occurrence of a coronary heart disease event, a cerebrovascular event, and/or intermittent claudication, by administering the above-described combination therapy to said at-risk persons.

A second object of the instant invention is to provide the above-described combination therapy to people who have clinical signs of atherosclerosis. Toward this end, the instant invention provides methods for halting or slowing the progression of atherosclerotic cardiovascular disease, coronary heart disease, ischemic heart disease, cerebrovascular disease and peripheral vessel disease, and preventing or reducing the risk of a first or subsequent occurrence of a coronary heart disease event, a cerebrovascular event, and/or intermittent claudication, by administering the above-described combination therapy to said persons who have clinically manifest atherosclerotic disease.

A third object of the instant invention involves the above-described methods further comprising the administration of one or more additional active agents either in separate or combined dosage formulations. A fourth object is to provide pharmaceutical compositions which can be used in the above-described methods. Additional objects will be evident from the following detailed description.

DETAILED DESCRIPTION OF THE INVENTION

The instant invention provides methods for preventing or reducing the risk of developing atherosclerosis, as well as for halting or slowing the progression of atherosclerotic disease once it has become clinically evident, comprising the administration of a therapeutically effective amount of an HMG-CoA RI in combination with a COX-2 inhibitor to a mammal who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The combination comprised of an HMG-CoA RI and a COX-2 inhibitor may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of an HMG-CoA reductase inhibitor in combination with a COX-2 inhibitor to a patient at risk for such an event. The patient may already have atherosclerotic disease at the time of administration, or may be at risk for developing it.

The instant invention also provides a method for treating, preventing, and/or reducing the risk of developing atherosclerosis and atherosclerotic disease events and reducing total cholesterol levels alone, or in conjunction with the treatment for a COX-2 mediated disease or disorder comprising the administration of a therapeutically effective amount of an HMG-CoA reductase inhibitor in combination with a COX-2 inhibitor to a patient in need of such treatment. COX-2 mediated diseases and disorders includes inflammatory diseases susceptible to treatment with a non-steroidal anti-inflammatory agent, arthritis including rheumatoid arthritis, and degenerative joint diseases (osteoarthritis).

Persons to be treated with the instant combination therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No. 93-3095, September 1993; abbreviated version: Expert Panel on Detection, Evaluation, and Treatment of High Blood Cholesterol in Adults, Summary of the second report of the national cholesterol education program (NCEP) Expert Panel on Detection, Evaluation, and Treatment of High Blood Cholesterol in Adults (Adult Treatment Panel II), JAMA, 1993, 269, pp. 3015–23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

A compound which inhibits HMG-CoA reductase is used in combination with a COX-2 inhibitor to practice the instant invention. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33.

Examples of HMG-CoA reductase inhibitors that may be used include but are not limited to lovastatin (MEVACOR®; see U.S. Pat. No. 4,231,938), simvastatin (ZOCOR®; see U.S. Pat. No. 4,444,784), pravastatin (PRAVACHOL®; see U.S. Pat. No. 4,346,227), fluvastatin (LESCOL®; see U.S. Pat. No. 5,354,772), atorvastatin (LIPITOR®; see U.S. Pat. No. 6,273,995) and cerivastatin (also known as rivastatin; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry &

Industry, pp. 85–89 (Feb. 5, 1996). The term HMG-CoA reductase inhibitor is intended to include all pharmaceutically acceptable salt, ester and lactone forms of compounds which have HMG-CoA reductase inhibitory activity, and therefor the use of such salts, esters and lactone forms is included within the scope of this invention. Preferably, the HMG-CoA RI is selected from lovastatin and simvastatin, and most preferably simvastatin.

Herein, the term "pharmaceutically acceptable salts" shall mean non-toxic salts of the compounds employed in this invention which are generally prepared by reacting the free acid with a suitable organic or inorganic base. Examples of salt forms of HMG-CoA reductase inhibitors may include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, and valerate.

Ester derivatives of the described compounds may act as prodrugs which, when absorbed into the bloodstream of a warm-blooded animal, may cleave in such a manner as to release the drug form and permit the drug to afford improved therapeutic efficacy.

The terms "inhibitor of cyclooxygenase-2", "cyclooxygenase-2 inhibitor" and "COX-2 inhibitor" as used herein embrace compounds which selectively inhibit cyclooxygenase-2 over cyclooxygenase-1. Employing the human whole blood COX-1 assay and the human whole blood COX-2 assay described in C. Brideau et al, Inflamm. Res. 45: 68–74 (1996), herein incorporated by reference, preferably, the compounds have a cyclooxygenase-2 $IC_{50}$ of less than about 2 $\mu M$ in the human whole blood COX-2 assay, yet have a cyclooxygenase-1 $IC_{50}$ of greater than about 5 $\mu M$ in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

As explained in J. Talley, Exp. Opin. Ther. Patents (1997), 7(1), pp. 55–62, three distinct structural classes of selective COX-2 inhibitor compounds have been identified. One class is the methane sulfonanilide class of inhibitors, of which NS-398, flosulide, nimesulide and L-745,337 are example members.

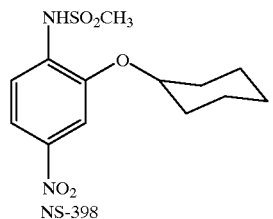

NS-398

-continued

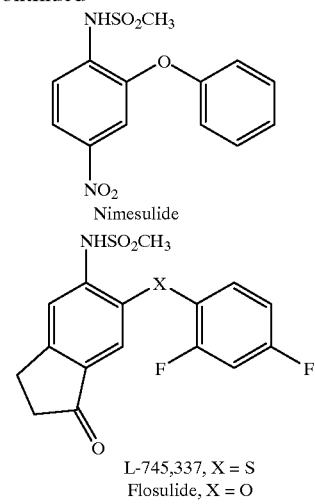

Nimesulide

L-745,337, X = S
Flosulide, X = O

A second class is the tricyclic inhibitor class, which can be further divided into the sub-classes of tricyclic inhibitors with a central carbocyclic ring (examples include SC-57666, 1, and 2); those with a central monocyclic heterocyclic ring (examples include DuP 697, SC-58125, SC-58635, and 3 (MK-966), 4 (L-748,706) and 5 (L-752,860)); and those with a central bicyclic heterocyclic ring (examples include 6, 7, 8, 9 and 10). Compounds 3, 4 and 5 are described in U.S. Pat. No. 5,474,995 (case 19028IA).

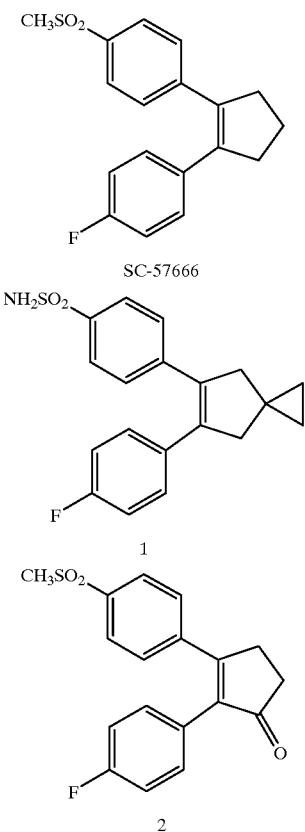

SC-57666

1

2

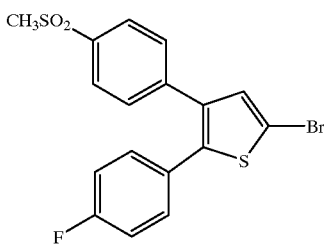
DuP 697
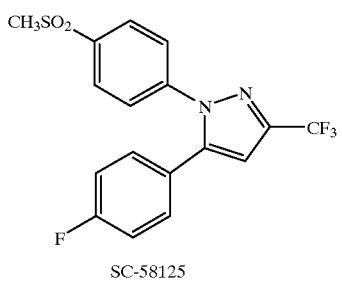
SC-58125
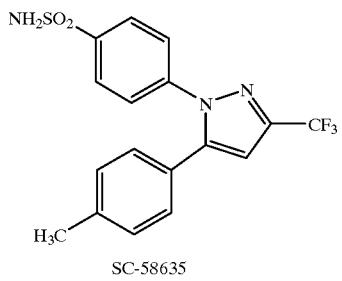
SC-58635
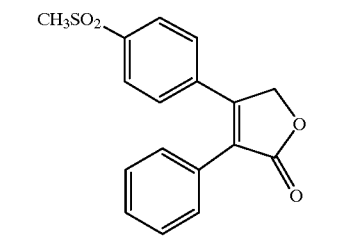
3
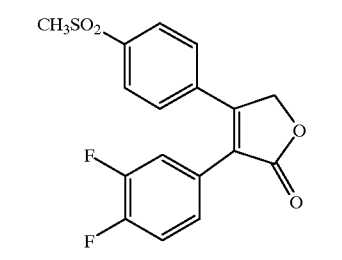
4
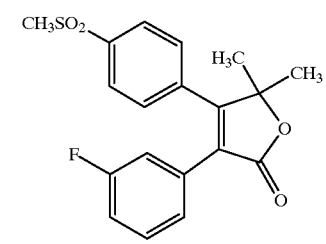
5
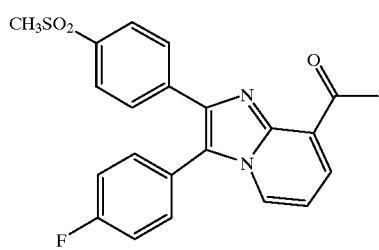
6
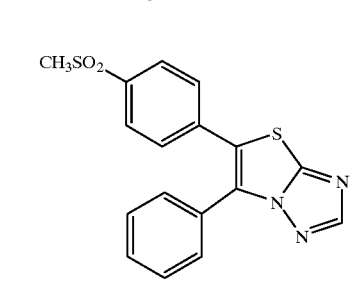
7
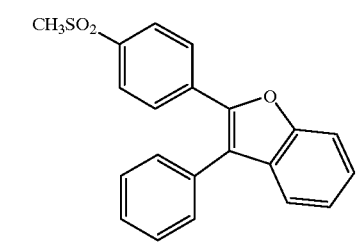
8
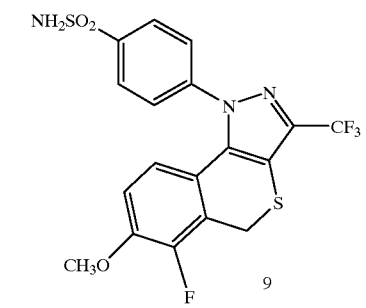
9
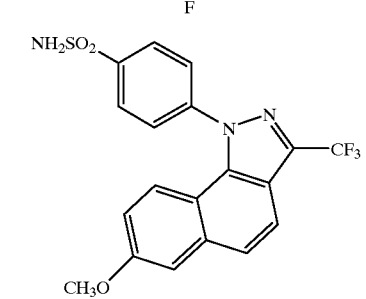
10
The third identified class can be referred to as those which are structurally modified NSAIDS, and includes L-761,066 and structure 11 as example members.

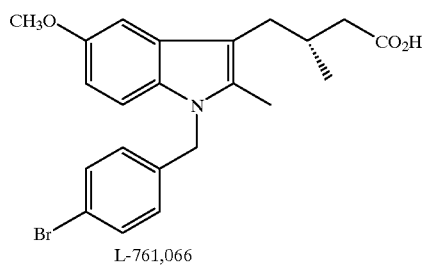

L-761,066

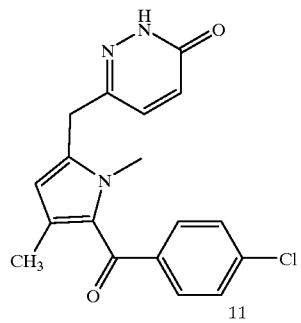

11

In addition to the structural classes, sub-classes, specific COX-2 inhibitor compound examples, and reference journal and patent publications described in the Talley publication which are all herein incorporated by reference, examples of compounds which selectively inhibit cyclooxygenase-2 have also been described in the following patent publications, all of which are herein incorporated by reference: U.S. Pat. Nos. 5,344,991, 5,380,738, 5,393,790, 5,409,944 (Case 18966), 5,434,178, 5,436,265 (Case 19080), 5,466,823, 5,474,995 (Case 19028IA), 5,510,368 (Case 19313), 5,536,752 (Case 19028DA), 5,550,142 (Case 19028DE), 5,552,422 (Case 19367), 5,604,253 (Case 19388), 5,604,260 (Case 18904IA), 5,639,780 (Case 19432); and International Patent Specification Nos. 94/13635, 94/15932, 94/20480, 94/26731, 94/27980, 95/00501, 95/15316, 96/03387, 96/03388, 96/06840; and International Publication Nos. WO 94/20480 (Case 1896Y), WO 96/21667 (Case 19367Y), WO 96/31509 (covers GR-253035), WO 96/36623 (Case 19456Y), WO 97/14691 (Case 19548Y), WO 97/16435 (Case 19563Y).

Additional COX-2 inhibitor compounds which are included in the scope of this invention include:

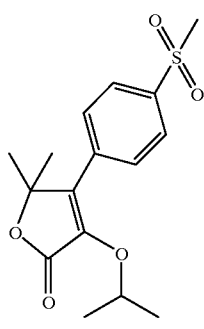

12
L-783,003
(19548Y, Ex 109a)

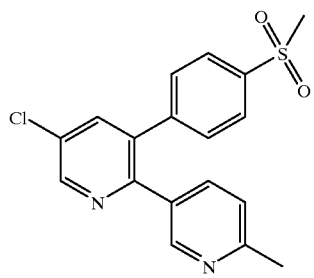

13
L-791,456
(966 back-up) (1976Y, Ex 23)

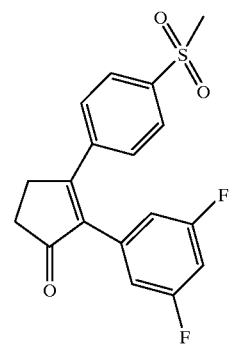

14
L-776,967
(back-up to 791,456)
(19028DA)

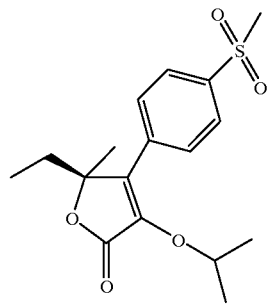

15
L-791,515
(19548Y, Ex 144)

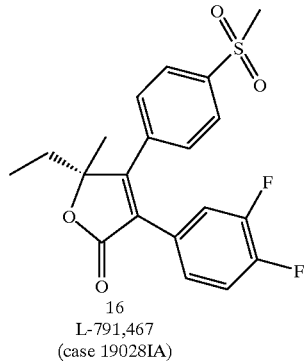

16
L-791,467
(case 19028IA)

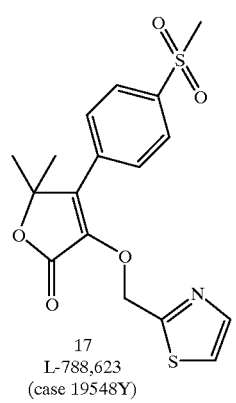
17
L-788,623
(case 19548Y)
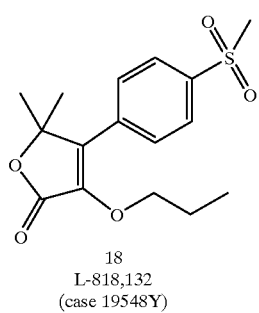
18
L-818,132
(case 19548Y)
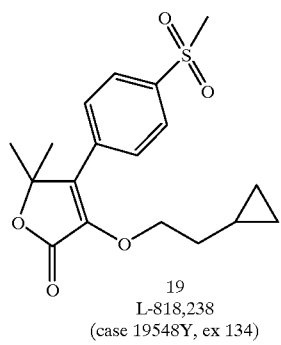
19
L-818,238
(case 19548Y, ex 134)
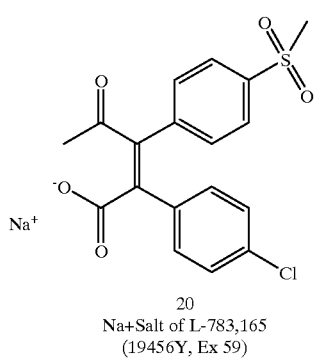
20
Na+Salt of L-783,165
(19456Y, Ex 59)
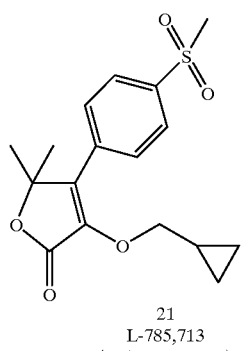
21
L-785,713
(19548Y, Ex 148)
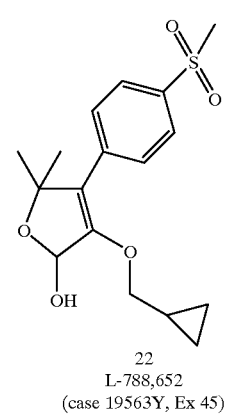
22
L-788,652
(case 19563Y, Ex 45)
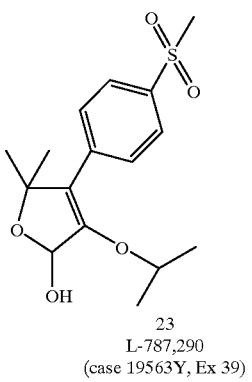
23
L-787,290
(case 19563Y, Ex 39)
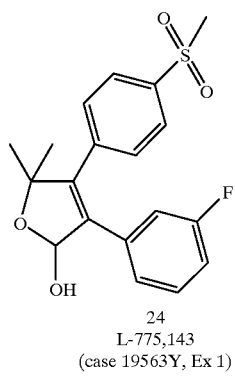
24
L-775,143
(case 19563Y, Ex 1)

-continued

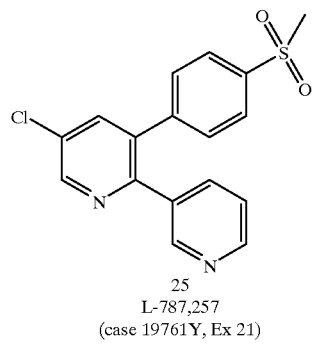

25
L-787,257
(case 19761Y, Ex 21)

Some of the compounds above can also be identified by the following chemical names:

3: 3-phenyl-4-4-(methylsulfonyl)phenyl)-2-(5H)-furanone (MK-966, case 19028IA, U.S. Pat. No. 5,474, 995, Ex 23);

4: 3-(3,4-difluorophenyl)-4-(4-(methylsulfonyl)phenyl)-2-(5H)-furanone (L-748,706, case 19028IA, U.S. Pat. No. 5,474,995, Ex 16);

5: 5,5-dimethyl-4-(4-(methylsulfonyl)phenyl)-3-(3-fluorophenyl)-5H-furan-2-one (L-752,860, case 19028IA, U.S. Pat. No. 5,474,995, Ex ?);

12: 5,5-dimethyl-4-(4-(methylsulfonyl)phenyl)-3-(2-propoxy)-5H-furan-2-one L-783,003 (case 19548Y, Ex 109a);

13: 5-chloro-3-(4-(methylsulfonyl)phenyl)-2-(2-methyl-5-pyridinyl)pyridine L-791,456 (back-up to 966) (case 19761Y, Ex 23);

14: 2-(3,5-difluorophenyl)-3-(4-(methylsulfonyl)phenyl)-2-cyclopenten-1-one L-776,967 (back-up to 791,456) (19028DA; in genus, no species);

15: 5(S)-5-ethyl-5-methyl-4-(4-(methylsulfonyl)phenyl)-3-(2-propoxy)-5H-furan-2-one L-791,515 (case 19548Y, Ex 144);

16: 5-ethyl-5-methyl-4-(4-(methylsulfonyl)phenyl)-3-(3,4-difluorophenyl)-5H-furan-2-one L-791, 467 (case 19028IA; in genus, no species);

17: 3-((2-thiazolyl)methoxy)-4-(4-(methylsulfonyl)phenyl)-5,5-dimethyl-5H-furan-2-one L-788,623 (case 19548Y PROBLEM -NOT IN CASE?);

18: 3-propyloxy-4-(4-(methylsulfonyl)phenyl)-5,5-dimethyl-5H-furan-2-one L-818,132 (case 19548Y; in genus, no species);

19: 3-(1-cyclopropylethoxy)-5,5-dimethyl-4-(4-methylsulfonyl)phenyl)-5H-furan-2-one L-818,238 (case 19548Y, ex. 134);

20: sodium 2-(4-chlorophenyl)-3-(4-(methylsulfonyl)phenyl)-4-oxo-2-pentenoate (case 19456Y; ex 59);

21: 3-(cyclopropylmethoxy)-5,5-dimethyl-4-(4-(methylsulfonyl)phenyl)-5H-furan-2-one L-785,713 (case 19548Y, Ex 148);

22: 3-(cyclopropylmethoxy)-5,5-dimethyl-4-(4-(methylsulfonyl)phenyl)-2,5-dihydrofuran-2-ol L-788,652 (case 19563Y, Ex 45);

23: 3-isopropoxy-5,5-dimethyl-4-(4-(methylsulfonyl)phenyl)-2,5-dihydrofuran-2-ol L-787,290 (case 19563Y, Ex 39);

24: 5,5-dimethyl-3-(3-fluorophenyl)-2-hydroxy-4-(4-(methylsulfonyl)phenyl)-2,5-dihydrofuran L-775,143 (case 19563Y, Ex 1);

25: 5-Chloro-3-(4-(methylsulfonyl)phenyl)-2-(3-pyridinyl)pyridine L-787,257 (case 19761Y, Ex 21).

The following publications describe and/or provide methods for making the compounds as indicated: compounds 12, 15, 17, 18, 19 and 21, WO 97/14691(19548Y); compounds 22, 23 and 24, WO 97/16435(19563Y); compound 20, WO 96/36623(19456Y); compound 14, U.S. Pat. No. 5,536,752 (19028DA); compound 16, U.S. Pat. No. 5,474,995 (19028IA). See Examples herein for compounds 13 and 25 (Case 19761Y, filed Jul. 11, 1997 not pubd yet).

Also incorporated herein by reference are those compounds described in WO 96/41645 as having structural Formula I, shown below, and the definition and preferred definitions and species described therein:

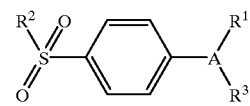

I

Particularly preferred compounds of formula (I) include:

5-(4-fluorophenyl)-1-[4-(methylsulfonyl)phenyl]-3-(trifluoromethyl)pyrazole;

4-(4-fluorophenyl)-5-[4-(methylsulfonyl)phenyl]-1-phenyl-3-(trifluoromethyl)pyrazole;

4-(5-(4-chlorophenyl)-3-(4-methoxyphenyl)-1H-pyrazol-1-yl)benzenesulfonamide;

4-(3,5-bis(4-methylphenyl)-1H-pyrazol-1-yl)benzenesulfonamide;

4-(5-(4-chlorophenyl)3-phenyl-1H-pyrazol-1-yl)benzenesulfonamide;

4-(3,5-bis(4-methoxyphenyl)-1H-pyrazol-1-yl)benzenesulfonamide;

4-(5-(4-chlorophenyl)-3-(4-methylphenyl)-1H-pyrazol-1-yl)benzenesulfonamide;

4-(5-(4-chlorophenyl)-3-(4-nitrophenyl)-1H-pyrazol-1-yl)benzenesulfonamide;

4-(5-(4-chlorophenyl)-3-(5-chloro-2-thienyl)-1H-pyrazol-1-yl)benzenesulfonamide;

4-(4-chloro-3,5-diphenyl-1H-pyrazol-1-yl)benzenesulfonamide;

4-(5-(4-chlorophenyl)-3-(trifluoromethyl)-1H-pyrazol-1-yl)benzenesulfonamide;

4-(5-phenyl)-3-(trifluoromethyl)-1H-pyrazol-1-yl)benzenesulfonamide;

4-(5-(4-fluorophenyl)-3-(trifluoromethyl)-1H-pyrazol-1-yl)benzenesulfonamide;

4-(5-(4-methoxyphenyl)-3-(trifluoromethyl)1H-pyrazol-1-yl)benzenesulfonamide;

4-(5-(4-chlorophenyl)-3-(difluoromethyl)-1H-pyrazol-1-yl)benzenesulfonamide;

4-(5-(4-methylphenyl)-3-(trifluoromethyl)-1H-pyrazol-1-yl)benzenesulfonamide;

4-(4-chloro-5-(4-chlorophenyl)-3-(trifluoromethyl)-1H-pyrazol-1-yl)benzenesulfonamide;

4-(3-(difluoromethyl)-5-(4-methylphenyl)-1H-pyrazol-1-yl)benzenesulfonamide;

4-(3-(difluoromethyl)-5-phenyl-1H-pyrazol-1-yl)benzenesulfonamide;

4-(3-(difluoromethyl)-5-(4-methoxyphenyl)-1H-pyrazol-1-yl)benzenesulfonamide;

4-(3-cyano-5-(4-fluorophenyl)-1H-pyrazol-1-yl)benzenesulfonamide;

4-(3-(difluoromethyl)-5-(3-fluoro-4-methoxyphenyl)-1H-pyrazol-1-yl)benzenesulfonamide;
4-(5-(3-fluoro-4-methoxyphenyl)-3-(trifluoromethyl)-1H-pyrazol-1-yl)benzenesulfonamide;
4-(4-chloro-5-phenyl-1H-pyrazol-1-yl)benzenesulfonamide;
4-(5-(4-chlorophenyl)-3-(hydroxyphenyl)-1H-pyrazol-1-yl)benzenesulfonamide;
4-(5-(4-(N,N-dimethylanino)phenyl)-3-(trifluoromethyl)-1H-pyrazol-1-yl)benzenesulfonamide;
5-(4-fluorophenyl)-6-(4-(methylsulfonyl)phenyl)spiro[2.4]hept-5-ene;
4-(6-(4-fluorophenyl)spiro[2.4]hept-5-en-5-yl)benzenesulfonamide;
6-(4-fluorophenyl)-7-(4-(methylsulfonyl)phenyl)spiro[3.4]oct-6-ene;
5-(3-chloro-4-methoxyphenyl)-6-(4-(methylsulfonyl)phenyl)spiro[2.4]hept-5-ene;
4-(6-(3-chloro-4-methoxyphenyl)spiro [2.4]hept-5-en-5-yl)benzenesulfonamide;
5-(3,5-dichloro-4-methoxyphenyl)-6-(4-(methylsulfonyl)phenyl)spiro[2.4]hept-5-ene;
5-(3-chloro-4-fluorophenyl)-6-(4-(methylsulfonyl)phenyl)spiro[2.4]hept-5-ene;
4-(6-(3,4-dichlorophenyl)spiro[2.4]hept-5-en-5-yl)benzenesulfonamide;
2-(3-chloro-4-fluorophenyl)-4-(4-fluorophenyl)-5-(4-methylsulfonylphenyl)thiazole;
2-(2-chlorophenyl)-4-(4-fluorophenyl)-5-(4-methylsulfonylphenyl)thiazole;
5-(4-fluorophenyl)-4-(4-methylsulfonylphenyl)-2-methylthiazole;
4-(4-fluorophenyl)-5-(4-methylsulfonylphenyl)-2-trifluoromethylthiazole;
4-(4-fluorophenyl)-5-(4-methylsulfonylphenyl)-2-(2-thienyl)thiazole;
4-(4-fluorophenyl)-5-(4-methylsulfonylphenyl)-2-benzylaminothiazole;
4-(4-fluorophenyl)-5-(4-methylsulfonylphenyl)-2-(1-propylamino)thiazole;
2-((3,5-dichlorophenoxy)methyl)-4-(4-fluorophenyl)-5-(4-(methylsulfonyl)phenyl)thiazole;
5-(4-fluorophenyl)-4-(4-methylsulfonylphenyl)-2-trifluoromethylthiazole;
1-methylsulfonyl-4-(1,1-dimethyl-4-(4-fluorophenyl)cyclopenta-2,4-dien-3-yl)benzene;
4-(4-(4-fluorophenyl)-1,1-dimethylcyclopenta-2,4-dien-3-yl)benzenesulfonamide;
5-(4-fluorophenyl)-6-(4-(methylsulfonyl)phenyl)spiro[2.4]hepta-4,6-diene;
4-(6-(4-fluorophenyl)spiro[2.4]hepta-4,6-dien-5-yl)benzenesulfonamide;
6(4-fluorophenyl)-2-methoxy-5-(4-(methylsulfonyl)phenyl)-pyridine-3-carbonitrile;
2-bromo-6-(4-fluorophenyl)-5-(4-(methylsulfonyl)phenyl)-pyridine-3-carbonitrile;
6-(4-fluorophenyl)-5-(4-(methylsulfonyl)phenyl)-2-phenyl-pyridine-3-carbonitrile;
4-(2-(4-methylpyridin-2-yl)-4-(trifluoromethyl)-1H-imidazol-1-yl)benzenesulfonamide;
4-(2-(5-methylpyridin-3-yl)-4-(trifluoromethyl)-1H-imidazol-1-yl)benzenesulfonamide;
4-(2-(2-methylpyridin-3-yl)-4-(trifluoromethyl)-1H-imidazol-1-yl)benzenesulfonamide;
3-(1-(4-(methylsulfonyl)phenyl)-4-(trifluoromethyl)-1H-imidazol-2-yl)benzenesulfonamide;
2-(1-(4-(methylsulfonyl)phenyl)-4-(trifluoromethyl)-1H-imidazol-2-yl)pyridine;
2-methyl-4-(1-(4-(methylsulfonyl)phenyl)-4-(trifluoromethyl)-1H-imidazol-2-yl)pyridine;
2-methyl-6-(1-(4-(methylsulfonyl)phenyl)-4-(trifluoromethyl)-1H-imidazol-2-yl)pyridine;
4-(2-(6-methylpyridin-3-yl)-4-(trifluoromethyl)-1H-imidazol-1-yl)benzenesulfonamide;
2-(3,4-difluorophenyl)-1-(4-(methylsulfonyl)phenyl)-4-(trifluoromethyl)-1H-imidazole;
4-(2-(4-methylphenyl)-4-trifluoromethyl)-1H-imidazol-1-yl)benzenesulfonamide;
2-(4-chlorophenyl)-1-(4-(methylsulfonyl)phenyl)-4-methyl-1H-imidazole;
2-(4-chlorophenyl)-1-(4-(methylsulfonyl)phenyl)-4-phenyl- 1H-imidazole;
2-(4-chlorophenyl)-4-(4-fluorophenyl)-1-(4-(methylsulfonyl)phenyl)-1H-imidazole;
2-(3-fluoro-4-methoxyphenyl)-1-(4-(methylsulfonyl)phenyl)-4-(trifluoromethyl)-1H-imidazole;
1-(4-(methylsulfonyl)phenyl)-2-phenyl-4-trifluoromethyl- 1H-imidazole;
2-(4-methylphenyl)-1-(4-(methylsulfonyl)phenyl)-4-trifluoromethyl-1H-imidazole;
4-(2-(3-chloro-4-methylphenyl)-4-(trifluoromethyl)-1H-imidazol-1-yl)benzenesulfonamide;
2-(3-fluoro-5-methylphenyl)-1-(4-(methylsulfonyl)phenyl)-4-(trifluoromethyl)-1H-imidazole;
4-(2-(3-fluoro-5-methylphenyl)-4-(trifluoromethyl)-1H-imidazol-1-yl)benzenesulfonamide;
2-(3-methylphenyl)-1-(4-(methylsulfonyl)phenyl)-4-(trifluoromethyl)-1H-imidazole;
4-(2-(3-methylphenyl)-4-(trifluoromethyl)-1H-imidazol-1-yl)benzenesulfonamide;
1-(4-(methylsulfonyl)phenyl)-2-(3-chlorophenyl)-4-(trifluoromethyl)-1H-imidazole;
4-(2-(3-chlorophenyl)4-(trifluoromethyl)-1H-imidazol-1-yl)benzenesulfonamide;
4-(2-phenyl-4-(trifluoromethyl)-1H-imidazol-1-yl)benzenesulfonamide;
4-(2-(4-methoxy-3-chlorophenyl)-4-(trifluoromethyl)-1H-imidazol-1-yl)benzenesulfonamide;
1-allyl-4-(4-fluorophenyl)-3-(4-(methylsulfonyl)phenyl)-5-(trifluoromethyl)-1H-pyrazole;
4-(1-ethyl-4-(4-fluorophenyl)-5-(trifluoromethyl)-1H-pyrazol-3-yl)benzenesulfonamide;
N-phenyl-(4-(4-fluorophenyl)-3-(4-(methylsulfonyl)phenyl)-5-(trifluoromethyl)-1H-pyrazol-1-yl)acetamide;
ethyl (4-(4-fluorophenyl)-3-(4-(methylsulfonyl)phenyl)-5-(trifluoromethyl)-1H-pyrazol-1-yl)acetate;
4-(4-fluorophenyl)-3-(4-(methylsulfonyl)phenyl)-1-(2-phenylethyl)-1H-pyrazole;
4-(4-fluorophenyl)-3-(4-(methylsulfonyl)phenyl)- 1-(2-phenylethyl)-5-(trifluoromethyl)pyrazole;
1-ethyl-4-(4-fluorophenyl)-3-(4-(methylsulfonyl)phenyl)-5-(trifluoromethyl)-1H-pyrazole;
5-(4-fluorophenyl)-4-(4-(methylsulfonyl)phenyl)-2-(trifluoromethyl)-1H-imidazole;

4-(4-(methylsulfonyl)phenyl)-5-(2-thiophenyl)-2-(trifluoromethyl)-1H-imidazole;
5-(4-fluorophenyl)-2-methoxy-4-(4-(methylsulfonyl)phenyl)-6-(trifluoromethyl)pyridine;
2-ethoxy-5-(4-fluorophenyl)-4-(4-(methylsulfonyl)phenyl)-6-(trifluoromethyl)pyridine;
5-(4-fluorophenyl)-4-(4-(methylsulfonyl)phenyl)-2-(2-propynyloxy)-6-(trifluoromethyl)pyridine;
2-bromo-5-(4-fluorophenyl)-4-(4-(methylsulfonyl)phenyl)-6-(trifluoromethyl)pyridine;
4-(2-(3-chloro-4-methoxyphenyl)-4,5-difluorophenyl)benzenesulfonamide;
1-(4-fluorophenyl)-2-(4-(methylsulfonyl)phenyl)benzene;
5-difluoromethyl-4-(4-(methylsulfonyl)phenyl)-3-phenylisoxazole;
4-(3-ethyl-5-phenylisoxazol-4-yl)benzenesulfonamide;
4-(5-difluoromethyl-3-phenylisoxazol-4-yl)benzenesulfonamide;
4-(5-hydroxymethyl-3-phenylisoxazol-4-yl)benzenesulfonamide;
4-(5-methyl-3-phenylisoxazol-4-yl)benzenesulfonamide;
1-(2-(4-fluorophenyl)cyclopenten-1-yl)-4-(methylsulfonyl)benzene;
1-(2-(4-fluoro-2-methylphenyl)cyclopenten-1-yl)-4-(methylsulfonyl)benzene;
1-(2-(4-chlorophenyl)cyclopenten-1-yl)-4-(methylsulfonyl)benzene;
1-(2-(2,4-dichlorophenyl)cyclopenten-1-yl)-4-(methylsulfonyl)benzene;
1-(2-(4-trifluoromethylphenyl)cyclopenten-1-yl)-4-(methylsulfonyl)benzene;
1-(2-(4-methylthiophenyl)cyclopenten-1-yl)-4-(methylsulfonyl)benzene;
1-(2-(4-fluorophenyl)-4,4-dimethylcyclopenten-1-yl)-4-(methylsulfonyl)benzene;
4-(2-(4-fluorophenyl)-4,4-dimethylcyclopenten-1-yl)benzenesulfonamide;
1-(2-(4-chlorophenyl)-4,4-dimethylcyclopenten-1-yl)-4-(methylsulfonyl)benzene;
4-(2-(4-chlorophenyl)-4,4-dimethylcyclopenten-1-yl)benzenesulfonamide;
4-(2-(4-fluorophenyl)cyclopenten-1-yl)benzenesulfonamide;
4-(2-(4-chlorophenyl)cyclopenten-1-yl)benzenesulfonamide;
1-(2-(4-methoxyphenyl)cyclopenten-1-yl)-4-(methylsulfonyl)benzene;
1-(2-(2,3-difluorophenyl)cyclopenten-1-yl)-4-(methylsulfonyl)benzene;
4-(2-(3-fluoro-4-methoxyphenyl)cyclopenten-1-yl)benzenesulfonamide;
1-(2-(3-chloro-4-methoxyphenyl)cyclopenten-1-yl)-4-(methylsulfonyl)benzene;
4-(2-(3-chloro-4-fluorophenyl)cyclopenten-1-yl)benzenesulfonamide;
4-(2-(2-methylpyridin-5-yl)cyclopenten-1-yl)benzenesulfonamide;
ethyl 2-(4-(4-fluorophenyl)-5-(4-(methylsulfonyl)phenyl)oxazol-2-yl)-2-benzyl-acetate;
2-(4-(4-fluorophenyl)-5-(4-(methylsulfonyl)phenyl)oxazol-2-yl)acetic acid;
2-(tert-butyl)-4-(4-fluorophenyl)-5-(4-(methylsulfonyl)phenyl)oxazole;
4-(4-fluorophenyl)-5-(4-(methylsulfonyl)phenyl)-2-phenyloxazole;
4-(4-fluorophenyl)-2-methyl-5-(4-(methylsulfonyl)phenyl)oxazole; and
4-(5-(3-fluoro-4-methoxyphenyl)-2-trifluoromethyl-4-oxazolyl)benzenesulfonamide; or a pharmaceutically acceptable salt thereof.

The compounds of use in this invention may have one or more chiral centers and the present compounds may occur as racemates, racemic mixtures and as individual diasteriomers or enantiomers with all such isomeric forms and mixtures thereof being included within the scope of this invention. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates, as well as anhydrous compositions, are encompassed within the scope of this invention. Some of the compounds described herein may contain olefinic double bonds, and unless specified otherwise, are meant to include both E and Z geometric isomers.

The COX-2 inhibitors that may be used with this invention encompass all pharmaceutically acceptable salt forms of the compounds. Examples of such salt forms of COX-2 inhibitors include but are not limited to salts derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The instant pharmaceutical combination comprising an HMG-CoA reductase inhibitor in combination with a COX-2 inhibitor includes administration of a single pharmaceutical dosage formulation which contains both the HMG-CoA reductase inhibitor and the COX-2 inhibitor, as well as administration of each active agent in its own separate pharmaceutical dosage formulation. Where separate dosage formulations are used, the HMG-CoA reductase inhibitor and the COX-2 inhibitor can be administered at essentially the same time, i.e., concurrently, or at separately staggered times, i.e, sequentially. The instant pharmaceutical combination is understood to include all these regimens. Administration in these various ways are suitable for the present invention as long as the beneficial pharmaceutical effect of the HMG-CoA reductase inhibitor and the COX-2 inhibitor are realized by the patient at substantially the same time. Such beneficial effect is preferably achieved when the target blood level concentrations of each active drug are maintained at substantially the same time. It is preferred that the HMG-CoA reductase inhibitor and the COX-2 inhibitor be co-administered concurrently on a once-a-day dosing schedule; however, varying dosing schedules, such as the HMG-CoA RI once per day and the COX-2 inhibitor once, twice or more times per day, is also encompassed herein. A single oral dosage formulation comprised of both an HMG-CoA reductase inhibitor and the COX-2 inhibitor is preferred. A single dosage formulation will provide convenience for the patient, which is an important consideration especially for patients who already have coronary heart disease and may be in need of multiple medications.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing an HMG-CoA RI in combination with COX-2 inhibitor is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

The term "patient" includes mammals, especially humans, who take an HMG-CoA reductase inhibitor in combination with a COX-2 inhibitor for any of the uses described herein. Administering of the drug combination to the patient includes both self-administration and administration to the patient by another person.

In particular, the daily dosage amounts of the HMG-CoA reductase inhibitor are intended to be the same or similar to those amounts which are employed for anti-hypercholesterolemic treatment and which are described in the Physicians' Desk Reference (PDR). For example, see the 50$^{th}$ Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA RI is from about 1 to 200 mg/day, and more preferably from about 5 to 160 mg/day. However, dosage amounts will vary depending on the potency of the specific HMG-CoA reductase inhibitor used as well as other factors as noted above. An HMG-CoA RI which has sufficiently greater potency may be given in sub-milligram daily dosages. The HMG-CoA reductase inhibitor may be administered from 1 to 4 times per day, and preferably once per day.

As examples, the daily dosage amount for simvastatin may be selected from 5 mg, 10 mg, 20 mg, 40 mg, 80 mg and 160 mg; for lovastatin, 10 mg, 20 mg, 40 mg and 80 mg; for fluvastatin sodium, 20 mg, 40 mg and 80 mg; for pravastatin sodium, 10 mg, 20 mg, and 40 mg; and for atorvastatin calcium, 10 mg, 20 mg, and 40 mg.

The inhibitor of cyclooxygenase-2 may be administered at a dosage level up to conventional dosage levels for NSAIDs.

Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

Additional active agents may be used in combination with the HMG-CoA RI and COX-2 inhibitor in a single dosage formulation, or may be administered to the patient in a separate dosage formulation, which allows for concurrent or sequential administration. One or more additional active agents may be administered with the HMG-CoA RI and COX-2 inhibitor. The additional active agent or agents can be cholesterol lowering compounds. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; platelet aggregation inhibitors, for example glycoprotein IIb/IIIa fibrinogen receptor antagonists and aspirin; vitamin $B_6$ (also known as pyridoxine) and the pharmaceutically acceptable salts thereof such as the HCl salt; vitamin $B_{12}$ (also known as cyanocobalamin); beta-blockers; folic acid or a pharmaceutically acceptable salt or ester thereof such as the sodium salt and the methylglucamine salt; and anti-oxidant vitamins such as vitamin C and E and beta carotene.

Examples of HMG-CoA synthase inhibitors include: the beta-lactone derivatives disclosed in U.S. Pat. No. 4,806,564, 4,816,477, 4,847,271, and 4,751,237; the beta lactam derivatives disclosed in U.S. Pat. No. 4,983,597 and the substituted oxacyclopropane analogues disclosed in European Patent Publication EP 0 411 703. The squalene synthetase inhibitors suitable for use herein include, but are not limited to, those disclosed by Biller et al., J. Med. Chem., 1988 Vol. 31, No. 10, pp. 1869–1871, including isoprenoid (phosphinylmethyl)-phosphonates such as those of the formula

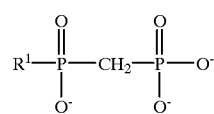

I

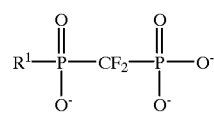

II wherein $R^1$ is:

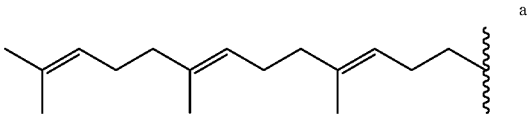

a

-continued

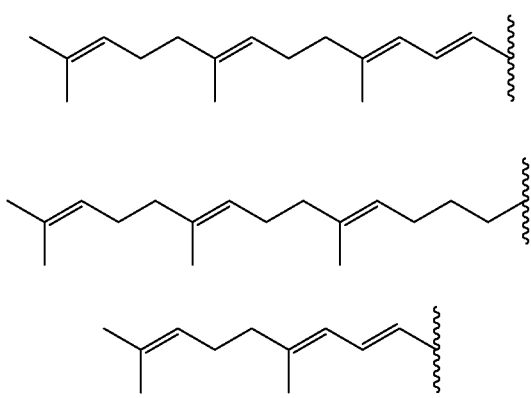

including the triacids thereof, triesters thereof and tripotassium and trisodium salts thereof as well as other squalene synthetase inhibitors disclosed in pending U.S. Pat. Nos. 4,871,721 and 4,924,024 and in Biller et al., J. Med.Chem., 1988, Vol. 31, No. 10, pp. 1869 to 1871.

In addition, other squalene synthetase inhibitors suitable for use herein include the terpenoid pyrophosphates disclosed by P. Ortiz de Montellano et al., J. Med. Chem., 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonate reported by McClard, R. W. et al., J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Further, the benzodiazepine squalene synthase inhibitors described in EP O 567 026 to Takeda Chemical Industries, and the quinuclidinyl squalene synthase inhibitors described in PCT publications WO 94/03451, WO 93/09115, WO 93/21183, WO 93/21184, WO 93/24486, and U.S. Pat. No. 5,135,935, may be co-administered with the HMG-CoA RI plus COX-2 inhibitor combination of the present invention. In addition, the zaragozic acid type squalene synthase inhibitors as described in U.S. Pat. Nos. 5,284,758; 5,283,256; 5,262,435; 5,260,332; 5,264,593; 5,260,215; 5,258,401; 5,254,727; 5,256,689; 5,132,320; 5,278,067, and PCT Publications WO 92/12156; WO 92/12157; WO 92/12158; WO 92/12159; WO 92/12160; WO 93/18040; WO 93/18039; WO 93/07151; and European Patent Publications EP O 512 865, EP O 568 946; EP O 524,677 and EP O 450 812, as well as the acyclic tricarboxylic acid compounds of U.S. Pat. No. 5,254,727, may be employed.

Illustrative examples of squalene epoxidase inhibitors are disclosed in European Patent Publication EP O 318 860 and in Japanese Patent Publication JO2 169-571A. LDL-receptor gene inducer molecules are disclosed in U.S. Pat. No. 5,182,298.

Examples of bile acid sequestrants which may be employed in the present method include cholestyramine, colestipol, and poly[methyl-(3-trimethylaminopropyl) imino-trimethylene dihalide] and those disclosed in WO95/34585 to Geltex Pharmaceuticals, Inc. and EP O 622 078 assigned to Hisamitsu Pharmaceutical Co., Inc.

Examples of cholesterol absorption inhibitors which may be employed in the present method include those described in WO 95/18143 and WO 95/18144 both assigned to Pfizer Inc., and WO 94/17038, WO 95/08532 and WO 93/02048 each assigned to Schering Corp.

The additional active agents described above which may be employed along with the HMG-CoA RI and COX-2 inhibitor combination therapy can be used, for example, in amounts as indicated in the PDR or in amounts as indicated in the reference disclosures, as appropriate.

The active agents employed in the instant combination therapy can be administered in such oral forms as tablets, capsules (each of which includes sustained release or timed release formulations), pills, powders, granules, elixirs, tinctures, suspensions, syrups, and emulsions. The instant invention includes the use of both oral rapid-release and time-controlled release pharmaceutical formulations. A particular example of an oral time-controlled release pharmaceutical formulation is described in U.S. Pat. No. 5,366,738. Oral formulations are preferred. Such pharmaceutical compositions are known to those of ordinary skill in the pharmaceutical arts; for example, see Remington's Pharmaceutical Sciences, Mack Publishing Co., Easton, Pa.

In the methods of the present invention, the active agents are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

Although the active agents of the present method may be administered in divided doses, for example two or three times daily, a single daily dose of each of the HMG-CoA RI and the COX-2 inhibitor is preferred, with a single daily dose of both agents in a single pharmaceutical composition being most preferred.

The instant invention also encompasses a process for preparing a pharmaceutical composition comprising combining the HMG-CoA RI and the COX-2 inhibitor with a pharmaceutically acceptable carrier, as well as the pharmaceutical composition which is made by combining the HMG-CoA RI and the COX-2 inhibitor with a pharmaceutically acceptable carrier.

A therapeutically effective amount of an HMG-CoA RI and a COX-2 inhibitor can be used together for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of a COX-2 inhibitor in combination with about 1 mg to 200 mg of an HMG-CoA RI, or more particularly about 5 mg to 160 mg of the HMG-CoA RI. More specific amounts of HMG-CoA RI which may be used in the medicament preparation include 1 mg, 5 mg, 10 mg, 20 mg, 40 mg, 80 mg, and 160 mg, as well as sub-milligram amounts of HMG-CoA RI's which have sufficient potency at such levels. As a further example, the medicament may be comprised of an HMG-CoA RI in combination with about 0.1 to 20 mg of a COX-2 inhibitor.

The instant invention also encompasses the use of an HMG-CoA reductase inhibitor for the preparation of a medicament for the combined use with a cyclooxygenase-2 inhibitor for preventing or reducing the risk of developing atherosclerotic disease, for halting or slowing the progression of atherosclerotic disease, or for preventing or reducing the risk of occurrence or recurrence of an atherosclerotic disease event; and the use of a cyclooxygenase-2 inhibitor for the preparation of a medicament for the combined use with an HMG-CoA reductase inhibitor for preventing or reducing the risk of developing atherosclerotic disease, for halting or slowing the progression of atherosclerotic disease, or for preventing or reducing the risk of occurrence or recurrence of an atherosclerotic disease event. The medicament or pharmaceutical combination comprised of the HMG-CoA RI and the COX-2 inhibitor may also be prepared with one or more additional active agents, such as those described supra.

Examples of dosage formulations suitable for use in practicing the instant invention follow.

EXAMPLE 1

| Ingredient | Amount per tablet |
|---|---|
| Simvastatin | 5.0 mg |
| BHA | 0.02 mg |
| Ascorbic acid | 2.50 mg |
| Citric acid | 1.25 mg |
| Microcrystalline cellulose | 5.0 mg |
| Pregel starch | 10.0 mg |
| Magnesium stearate | 0.5 mg |
| Lactose | 74.73 mg |

All the ingredients except magnesium stearate are blended together in a suitable mixer. The powder mixture is then granulated with adequate quantities of granulating solvent(s). The wet granulated mass is dried in a suitable dryer. The dried granulation is sized through a suitable screen. The sized granulation is mixed with magnesium stearate before tableting. The tablets may be coated if deemed necessary. Additional ingredients that may be added to the above include suitable color and mixtures of colors.

EXAMPLE 2

| Ingredient | Amount per tablet |
|---|---|
| Simvastatin | 5.0 mg |
| BHA | 0.04 mg |
| Citric acid | 2.5 mg |
| Microcrystalline cellulose | 10.0 mg |
| Pregel starch | 20.0 mg |
| Magnesium stearate | 1.0 mg |
| Lactose | 148.46 mg |
| Hydrolized gelatin | 8.0 mg |

The process of manufacture is essentially the same as in Example 1, above.

EXAMPLE 3

| Ingredient | Amount per tablet |
|---|---|
| Simvastatin | 80.0 mg |
| BHA | 0.16 mg |
| Ascorbic acid | 20.0 mg |
| Citric acid | 10.0 mg |
| Microcrystalline cellulose | 40.0 mg |
| Pregel starch | 80.0 mg |
| Lactose | 550.0 mg |
| Colorant | 5.0 mg |
| Magnesium stearate | 4.8 mg |

The process of manufacture is essentially the same as in Example 1, above.

EXAMPLE 4

| Amount per tablet | Ingredient |
|---|---|
| 25 mg | COX-2 Inhibitor |
| 79.7 mg | Microcrystalline cellulose |
| 79.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Tablet dose strengths of between 5 and 125 mg can be accomodated by varying total tablet weight, and the ratio of the first three ingredients. Generally it is preferable to maintain a 1:1 ratio for microcrystalline cellulose:lactose monohydrate.

EXAMPLE 4A

Wet granulated tablet composition

| Amount per tablet | Ingredient |
|---|---|
| 12.5 mg | COX-2 Inhibitor |
| 86 mg | Microcrystalline cellulose |
| 86 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 4B

Wet granulated tablet composition

| Amount per tablet | Ingredient |
|---|---|
| 10 mg | COX-2 Inhibitor |
| 87.2 mg | Microcrystalline cellulose |
| 87.2 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 4C

Wet granulated tablet composition

| Amount per tablet | Ingredient |
|---|---|
| 5 mg | COX-2 Inhibitor |
| 89.7 mg | Microcrystalline cellulose |
| 89.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 5

Directly compressed tablet composition

| Amount per tablet | Ingredient |
|---|---|
| 25 mg | COX-2 Inhibitor |
| 106.9 mg | Microcrystalline cellulose |
| 106.9 mg | Lactose anhydrate |
| 7.5 mg | Crosmellose sodium |
| 3.7 mg | Magnesium stearate |

Tablet dose strengths of between 5 and 125 mg can be accomodated by varying total tablet weight, and the ratio of the first three ingredients. Generally it is preferable to maintain a 1:1 ratio for microcrystalline cellulose:lactose monohydrate.

EXAMPLE 5A

Directly compressed tablet composition

| Amount per tablet | Ingredient |
|---|---|
| 12.5 mg | COX-2 Inhibitor |
| 113.2 mg | Microcrystalline cellulose |
| 113.2 mg | Lactose anhydrate |
| 7.5 mg | Croscarmellose sodium |
| 3.7 mg | Magnesium stearate |

EXAMPLE 5B

Directly compressed tablet composition

| Amount per tablet | Ingredient |
|---|---|
| 10 mg | COX-2 Inhibitor |
| 42.5 mg | Microcrystalline cellulose |
| 42.5 mg | Lactose anhydrate |
| 4 mg | Croscarmellose sodium |
| 1 mg | Magnesium stearate |

EXAMPLE 5C

Directly compressed tablet composition

| Amount per tablet | Ingredient |
|---|---|
| 5 mg | COX-2 Inhibitor |
| 45 mg | Microcrystalline cellulose |
| 45 mg | Lactose anhydrate |
| 4 mg | Croscarmellose sodium |
| 1 mg | Magnesium stearate |

EXAMPLE 6

Hard gelatin capsule composition

| Amount per capsule | Ingredient |
|---|---|
| 25 mg | COX-2 Inhibitor |
| 37 mg | Microcrystalline cellulose |
| 37 mg | Lactose anhydrate |
| 1 mg | Magnesium stearate |
| 1 capsule | Hard gelatin capsule |

Capsule dose strengths of between 1 and 50 mg can be accomodated by varying total fill weight, and the ratio of the first three ingredients. Generally it is preferable to maintain a 1:1 ratio for microcrystalline cellulose:lactose monohydrate.

EXAMPLE 7

Oral solution

| Amount per 5 mL dose | Ingredient |
|---|---|
| 50 mg | COX-2 Inhibitor |
| to 5 mL with Polyethylene oxide 400 | |

Solution dose strengths of between 1 and 50 mg/5 mL can be accomodated by varying the ratio of the two ingredients.

EXAMPLE 8

Oral suspension

| Amount per 5 mL dose | Ingredient |
| --- | --- |
| 101 mg | COX-2 Inhibitor |
| 150 mg | Polyvinylpyrrolidone |
| 25 mg | Poly oxyethylene sorbitan monolaurate |
| 10 mg | Benzoic acid |
| to 5 mL with sorbitol solution (70%) | |

Suspension dose strengths of between 1 and 50 mg/5 ml can be accomodated by varying the ratio of the first two ingredients.

EXAMPLE 9

Intravenous infusion

| Amount per 200 mL dose | Ingredient |
| --- | --- |
| 1 mg | COX-2 inhibitor |
| 0.2 mg | Polyethylene oxide 400 |
| 1.8 mg | Sodium chloride |
| to 200 mL | Purified water |

EXAMPLE 10

5-Chloro-3-(4-methylsulfonyl)phenyl-2-(2-methyl-5-pyridinyl)pyridine (Compund 13)

Step 1: Trifluoromethanesulfonic acid 2-methylpyridin-5-yl ester

To a mixture of 5-hydroxy-2-methylpyridine (2 g) and pyridine (1.9 mL) in dichloromethane (100 mL) at 0° C. was added trifluoromethanesulfonic acid anhydride (3.4 mL). The mixture was stirred at this temperature for 15 min and then at r.t. for 45 min. Ammonium acetate (25%) was added and the organics were removed and washed with 1N HCl, dried and concentrated. The title compound was obtained as a beige liquid (4 g) that was used as such.

Step 2: 2-Methyl-5-trimethylstannylpyridine

A mixture of trifluoromethanesulfonic acid 2-methylpyridin-5-yl ester (2.1 g), hexamethylditin (2.85 g), lithium chloride (1.1 g) and palladium tetrakis(triphenylphosphine) (190 mg) was heated at reflux for 180 min and then cooled to r.t. The mixture was filtered through a bed of celite, washing with ethyl acetate. The filtrate was washed twice with 5% potassium fluoride, dried and concentrated. Flash chromatography (eluting with hexane/ethyl acetate, 6:1 v/v) of the residue provided the title compound as a pale yellow oil (1.3 g).

Step 3: 5-Chloro-3-(4-methylsulfonyl)phenyl-2-(2-methyl-5-pyridyl)pyridine

A mixture of 2,5-dichloro-3-(4-methylsulfonyl)phenyl-pyridine from Example 20, Step 5 (750 mg), 2-methyl-5-trimethyl-stannylpyridine (1.3 g) and palladium tetrakis(triphenylphosphine) (290 mg) in NMP (10 mL) was heated at 100° C. for 15 h. The mixture was cooled to r.t., diluted with ethyl acetate and filtered through a bed of celite. The filtrate was washed with water, twice with 5% potassium fluoride and then extracted with 1 N HCl. The aqueous phase was neutralized with 10 N sodium hydroxide and then extracted with ethyl acetate. The organics were concentrated and the residue subjected to flash chromatography (eluting with ethyl acetate) to provide the title compound as a white solid, m.p. 127–128° C.

EXAMPLE 11

5-Chloro-3-(4-methylsulfonyl)phenyl-2-(2-pyridinyl)pyridine

Step 1: 3-Bromo-5-chloro-2-hydroxypyridine

A mixture of 5-chloro-2-hydroxypyridine (100 g) and bromine (40.1 mL) in acetic acid (400 mL) was stirred at r.t. for 1 h. The mixture was poured into 3 L of water and stirred for 30 min then filtered. The residual solid was washed with 2 L of cold water, air dried and then coevaporated with toluene three times and with benzene two times. The white solid (81 g) so obtained was used in the subsequent reaction.

Step 2: 2-Benzyloxy-3-bromo-5-chloropyridine

A mixture of 3-bromo-5-chloro-2-hydroxypyridine (81 g), benzyl bromide (52 mL) and silver carbonate (97 g) in benzene (1 L) was heated at 70° C. for 1 h. The mixture was cooled to r.t. and then filtered through a bed of celite. The filtrate was concentrated and the residual off-white solid was recrystallized from hexane to provide the title compound as a white solid (102 g).

Step 3: 2-Benzyloxy-5-chloro-3-(4-methylsulfonyl)phenylpyridine

Following the procedures described in Example 1, Steps 2 and 3, but substituting 2-benzyloxy-3-bromo-5-chloropyridine (81 g) from Step 2 for 2-amino-3-bromo-5-trifluoromethylpyridine, the title compound was obtained as a white solid (72 g).

Step 4: 5-Chloro-2-hydroxy-3-(4-methylsulfonyl)phenylpyridine

A solution of 2-benzyloxy-5-chloro-3-(4-methylsulfonyl)-phenylpyridine (72 g) in trifluoroacetic acid (250 mL) was stirred at 40° C. for 15 min and then poured into ice/water (~1 L). After stirring for 10 min, the white solid was filtered, washed twice with a further 1 L of water and then air dried to provide the title compound.

Step 5: 2.5-Dichloro-3-(4-methylsulfonyl)phenylpyridine

The crude 5-chloro-2-hydroxy-3-(4-methylsulfonyl)-phenylpyridine from Step 4 was heated in a sealed bomb at 150° C. with $POCl_3$ (400 mL) for 15 h. After cooling to r.t. the excess $POCl_3$ was removed by distillation under vacuum. The residue was diluted with ethyl acetate and water and then neutralized with sodium hydroxide (10 N) to ~pH 7. The organics were removed, washed with brine and concentrated. The residual solid was recrystallized from ether to provide the title compound as white solid (61 g).

Step 6: Lithium Tri-n-propoxy-2-pyridylbornonate

Following the procedures described in Example 15, Step 1 but substituting 2-bromopyridine (1.9 mL) for 3-bromopyridine, the title compound was prepared as an off-white solid (4.1 g).

Step 7: 5-Chloro-3-(4-methylsulfonyl)phenyl-2-(2-pyridinyl)-pyridine

A mixture of 2,5-dichloro-3-(4-methylsulfonyl)phenyl-pyridine (1 g), lithium tri-n-propoxy-2-pyridylboronate (1.22 g), sodium carbonate (5 mL, 2M) and bis(triphenylphosphine)palladium dibromide (520 mg) in toluene (100 mL), isopropanol (10 mL) and water (25 mL) was heated at reflux for 7 h. The mixture was cooled to r.t., diluted with ethyl acetate and filtered through a bed of celite. The filtrated was extracted with 6 N HCl and the aqueous was washed with ethyl acetate. The aqueous phase was basified to ~pH 10 with 10 N sodium hydroxide and then extracted with ethyl acetate. The organics were washed with brine, dried and concentrated. Flash chromatography (eluting with hexanelethyl acetate, 1:1 v/v) of the residue provided the title compound as a white solid, m.p. 134–135° C. (350 mg).

EXAMPLE 12
Lithium Tri-n-propoxy-3-pyridinylboronate

To a solution of 3-bromopyridine (39.5 g) in ether (800 mL) at −90° C. (internal temperature) was added n-BuLi (100 mL, 2.5 M) at a rate so that the internal temperature did not exceed −78° C. The resulting mixture was stirred for 1 h at −78° C. and then triisopropoxy-borate (59 mL) was added and the resulting mixture was warmed to 0° C. Methanol was added and the mixture was evaporated three times from methanol and then two times from n-propanol. The residue was pumped under high vacuum for 3 days and the resulting foam (76 g of a 1:1 mixture of the title compound:n-propanol) was used as such in the subsequent reaction.

EXAMPLE 13
5-Chloro-3-(4-methylsulfonyl)phenyl-2-(3-pyridinyl)pyridine (Compound 25)

Following the procedures described in Example 11, Step 7, but substituting lithium tri-n-propoxy-3-pyridinylboronate from Example 12 for lithium tri-n-propoxy-2-pyridinylboronate, the title compound was obtained as a white solid, m.p. 168–169° C.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for reducing the risk of developing atherosclerotic disease comprising the administration of a prophylactically effective amount of an HMG-CoA reductase inhibitor in combination with a prophylactically effective amount of an cyclooxygenase-2 inhibitor to a patient at risk of developing atherosclerotic disease.

2. The method of claim 1 wherein the atherosclerotic disease is selected from cardiovascular disease, cerebrovascular disease and peripheral vessel disease.

3. The method of claim 2 wherein the cardiovascular disease is coronary heart disease.

4. The method of claim 1 wherein the HMG-CoA reductase inhibitor is selected from lovastatin, simvastatin, pravastatin, fluvastatin, atorvastatin, cerivastatin and the pharmaceutically acceptable salt, ester and lactone forms thereof.

5. The method of claim 4 wherein the HMG-CoA reductase inhibitor is selected from lovastatin and simvastatin.

6. The method of claim 4 wherein the HMG-CoA reductase inhibitor is simvastatin.

7. The method of claim 1 wherein the COX-2 inhibitor is selected from:
5,5-dimethyl-4-(4(methylsulfonyl)phenyl)-3-(2-propoxy)-5H-furan-2-one (12);
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
5(S)-5-ethyl-5-methyl-4-(4-(methylsulfonyl)phenyl)-3-(2-propoxy)-5H-furan-2-one (15);
5-ethyl-5-methyl-4-(4-(methylsulfonyl)phenyl)-3-(3,4-difluorophenyl)-5H-furan-2-one (16);
3-((2-thiazolyl)methoxy)-4-(4-(methylsulfonyl)phenyl)-5,5-dimethyl-5H-furan-2-one (17);
3-propyloxy-4-(4-(methylsulfonyl)phenyl)-5,5-dimethyl-5H-furan-2-one (18);
3-(1-yclopropylethoxy)-5,5-dimethyl-4-(4-methylsulfonyl)phenyl)-5H-furan-2-one (19);
sodium 2-(4-chlorophenyl)-3-(4-(methylsulfonyl)phenyl)-4-oxo-2-pentenoate (20);
3-(cyclopropylmethoxy)-5,5-dimethyl-4-(4-(methylsulfonyl)phenyl)-5H-furan-2-one (21);
3-(cyclopropylmethoxy)-5,5-dimethyl-4-(4-(methylsulfonyl)phenyl)-2,5-dihydrofuran-2-ol (22);
3-isopropoxy-5,5-dimethyl-4-(4-(methylsulfonyl)phenyl)-2,5-dihydrofuran-2-ol (23);
5,5-Dimethyl-3-(3-fluorophenyl)-2-hydroxy-4-(4-(methylsulfonyl)phenyl)-2,5-dihydrofuran (24);
5-Chloro-3-(4-(methylsulfonyl)phenyl)-2-(3-pyridinyl)pyridine (25);
3-phenyl-4-(4-(methylsulfonyl)phenyl)-2-(5H)-furanone (3);
3-(3,4-difluorophenyl)-4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

8. The method of claim 7 wherein the COX-2 inhibitor is selected from:
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
3-phenyl-4-(4-(methylsulfonyl)phenyl)-2-(5H)-furanone (3);
3-(3,4-difluorophenyl)-4-(4(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

9. The method of claim 6 wherein the COX-2 inhibitor is 5-chloro-3-(4-(methylsulfonyl)phenyl)-2-(2-methyl-5-pyridinyl)pyridine (13) or a pharmaceutically acceptable salt thereof.

10. The method of claim 6 wherein the COX-2 inhibitor is 2-(3,5-difluorophenyl)-3-(4-(methylsulfonyl)phenyl)-2-cyclopenten-1-one (14) or a pharmaceutically acceptable salt thereof.

11. The method of claim 6 wherein the COX-2 inhibitor is 3-phenyl-4-(4-(methylsulfonyl)phenyl)-2-(5H)-furanone (3) or a pharmaceutically acceptable salt thereof.

12. The method of claim 6 where in the COX-2 inhibitor is 3-(3,4-difluorophenyl)-4-(4-(methylsulfonyl)phenyl)-2-(5H)-furanone (4) or a pharmaceutically acceptable salt thereof.

13. The method of claim 6 wherein the COX-2 inhibitor is 5,5-dimethyl-4-(4-(methylsulfonyl)phenyl)-3-(3-fuorophenyl)-5H-furan-2-one (5) or a pharmaceutically acceptable salt thereof.

14. The method of claim 1 further comprising the administration of a therapeutically effective amount of at least one additional active agent selected from an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequestrant, an LDL receptor inducer, a platelet aggregation inhibitor, vitamin $B_6$ and the pharmaceutically acceptable salts thereof, vitamin $B_{12}$, a beta-blocker, folic acid or a pharmaceutically acceptable salt or ester thereof, vitamin C, vitamin E and beta carotene.

15. A method for halting or slowing the progression of atherosclerotic disease comprising the administration of a therapeutically effective amount of an HMG-CoA reductase inhibitor in combination with a therapeutically effective amount of a cyclooxygenase-2 inhibitor to a patient who has atherosclerotic disease.

16. The method of claim 15 wherein the atherosclerotic disease is selected from cardiovascular disease, cerebrovascular disease and peripheral vessel disease.

17. The method of claim 16 wherein the cardiovascular disease is coronary heart disease.

18. The method of claim 15 wherein the HMG-CoA reductase inhibitor is selected from lovastatin, simvastatin, pravastatin, fluvastatin, atorvastatin, cerivastatin and the pharmaceutically acceptable salt, ester and lactone forms thereof.

19. The method of claim 18 wherein the HMG-CoA reductase inhibitor is selected from lovastatin and simvastatin.

20. The method of claim 19 wherein the HMG-CoA reductase inhibitor is simvastatin.

21. The method of claim 15 wherein the COX-2 inhibitor is selected from:
5,5-dimethyl-4-(4-(methylsulfonyl)phenyl)-3-(2-propoxy)-5H-furan-2-one (12);
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
5(S)-5-ethyl-5-methyl -4-(4-(methylsulfonyl)phenyl)-3-(2-propoxy)-5H-furan-2-one (15);
5-ethyl-5-methyl (4-(methylsulfonyl)phenyl)-3-(3,4-difluorophenyl)-5H-furan-2-one (16);
3-((2-thiazolyl)methoxy)-4-(4-(methylsulfonyl)phenyl)-5,5-dimethyl-5H-furan-2-one (17);
3-propyloxy-4-(4-(methylsulfonyl)phenyl)-5,5-dimethyl-5H-furan-2-one (18);
3-(1-cyclopropylethoxy)-5,5-dimethyl-4-(4-methylsulfonyl)phenyl)-5H-furan-2-one (19);
sodium 2-(4-chlorophenyl)-3-(4-(methylsulfonyl)phenyl)-4-oxo-2-pentenoate (20);
3-(cyclopropylmethoxy)-5,5-dimethyl-4-(4-(methylsulfonyl)phenyl)-5H-furan-2-one (21);
3-(cyclopropylmethoxy)-5,5-dimethyl-4-(4-(methylsulfonyl)phenyl)-2,5-dihydrofuran-2-ol (22);
3-isopropoxy-5,5-dimethyl-4-(4-(methylsulfonyl)phenyl)-2,5-dihydrofuran-2-ol (23);
5,5-Dimethyl-3-(3-fluorophenyl)-2-hydroxy-4-(4-(methylsulfonyl)phenyl)-2,5-dihydrofuran (24);
5-Chloro-3-(4-(methylsulfonyl)phenyl)-2-(3-pyridinyl)pyridine (25);
3-phenyl-4-(4-(methylsulfonyl)phenyl)-2-(5H)-furanone (3);
3-(3,4-difluorophenyl)-4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

22. The method of claim 21 wherein the COX-2 inhibitor is selected from:
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
3-phenyl-4-(4-(methylsulfonyl)phenyl)-2-(5H)-furanone (3);
3-(3,4-difluorophenyl)-4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

23. The method of claim 20 wherein the COX-2 inhibitor is 5-chloro-3-(4-(methylsulfonyl)phenyl)-2-(2-methyl-5-pyridinyl)pyridine (13) or a pharmaceutically acceptable salt thereof.

24. The method of claim 20 wherein the COX-2 inhibitor is 2-(3,5-difluorophenyl)-3-(4-(methylsulfonyl)phenyl)-2-cyclopenten-1-one (14) or a pharmaceutically acceptable salt thereof.

25. The method of claim 20 wherein the COX-2 inhibitor is 3-phenyl-4-(4-(methylsulfonyl)phenyl)-2-(5H)-furanone (3) or a pharmaceutically acceptable salt thereof.

26. The method of claim 20 wherein the COX-2 inhibitor is 3-(3,4-difluorophenyl)-4-(4-(methlylsulfonyl)phenyl)-2-(5H)-furanone (4) or a pharmaceutically acceptable salt thereof.

27. The method of claim 20 wherein the COX-2 inhibitor is 5,5-dimethyl-4-(4-(methylsulfonyl)phenyl)-3-(3-fluorophenyl)-5H-furan-2-one (5) or a pharmaceutically acceptable salt thereof.

28. The method of claim 15 further comprising the administration of a therapeutically effective amount of at least one additional active agent selected from an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequestrant, an LDL receptor inducer, a platelet aggregation inhibitor, vitamin $B_6$ and the pharmaceutically acceptable salts thereof, vitamin $B_{12}$, a beta-blocker, folic acid or a pharmaceutically acceptable salt or ester thereof, vitamin C, vitamin E and beta carotene.

29. A method for reducing the risk of occurrence or recurrence of an atherosclerotic disease event comprising the administration of a prophylactically effective amount of an HMG-CoA reductase inhibitor in combination with a prophylactically effective amount of a cyclooxygenase-2 inhibitor to a patient at risk of having an atherosclerotic disease event.

30. The method of claim 29 wherein the patient has atherosclerotic disease.

31. The method of claim 29 wherein the patient is at risk for developing atherosclerotic disease.

32. The method of claim 29 wherein the atherosclerotic disease event is selected from a coronary heart disease event, a cerebrovascular event and intermittent claudication.

33. The method of claim 32 wherein the coronary heart disease event is selected from coronary heart disease death, myocardial infarction, and coronary revascularization procedures.

34. The method of claim 32 wherein the cerebrovascular event is selected from a cerebrovascular accident and a transient ischemic attack.

35. The method of claim 29 wherein the HMG-CoA reductase inhibitor is selected from lovastatin, simvastatin, pravastatin, fluvastatin, atorvastatin, cerivastatin and the pharmaceutically acceptable salt, ester and lactone forms thereof.

36. The method of claim 35 wherein the HMG-CoA reductase inhibitor is selected from lovastatin and simvastatin.

37. The method of claim 36 wherein the HMG-CoA reductase inhibitor is simvastatin.

38. The method of claim 29 wherein the COX-2 inhibitor is selected from:
5,5-dimethyl-4-(4-(methylsulfonyl)phenyl)-3-(2-propoxy)-5H-furan-2-one (12);
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
5(S)-5-ethyl-5-methyl-4-(4-(methylsulfonyl)phenyl)-3-(2-propoxy)-5H-furan-2-one (15);
5-ethyl-5-methyl-4-(4-(methylsulfonyl)phenyl)-3-(3,4-difluorophenyl)-5H-furan-2-one (16);
3-((2-thiazolyl)methoxy)4-(4-(methylsulfonyl)phenyl)-5,5-dimethyl-5H-furan-2-one (17);
3-propyloxy-4-(4-(methylsulfonyl)phenyl)-5,5-dimethyl-5H-furan-2-one (18);
3-(1-cyclopropylethoxy)-5,5-dimethyl-4-(4-methylsulfonyl)phenyl)-5H-furan-2-one (19);
sodium 2-(4-chlorophenyl)-3-(4-(methylsulfonyl)phenyl)-4-oxo-2-pentenoate (20);
3-(cyclopropylmethoxy)-5,5-dimethyl-4-(4-(methylsulfonyl)phenyl)-5H-furan-2-one (21);
3-(cyclopropylmethoxy)-5,5-dimethyl-4-(4-(methylsulfonyl)phenyl)-2,5-dihydrofuran-2-ol (22);
3-isopropoxy-5,5-dimethyl-4-(4-(methylsulfonyl)phenyl)-2,5-dihydrofuran-2-ol (23);
5,5-Dimethyl-3-(3-fluorophenyl)-2-hydroxy-4-(4-(methylsulfonyl)phenyl)-2,5-dihydrofuran (24);
5-Chloro-3-(4-(methylsulfonyl)phenyl)-2-(3-pyridinyl)pyridine (25);
3-phenyl-4-(4-(methylsulfonyl)phenyl)-2-(5H)-furanone (3);
3-(3,4-difluorophenyl)4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

39. The method of claim 38 wherein the COX-2 inhibitor is selected from:
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
3-phenyl-4-(4-(methylsulfonyl)phenyl)-2-(5H)-furanone (3);
3-(3,4-difluorophenyl)-4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

40. The method of claim 37 wherein the COX-2 inhibitor is 5-chloro-3-(4-(methylsulfonyl)phenyl)-2-(2-methyl-5-pyridinyl)pyridine (13) or a pharmaceutically acceptable salt thereof.

41. The method of claim 37 wherein the COX-2 inhibitor is 2-(3,5diflorophenyl)-3-(4-(methylsulfonyl)phenyl)-2-cyclopenten-1-one (14) or a pharmaceutically acceptable salt thereof.

42. The method of claim 37 wherein the COX-2 inhibitor is 3-phenyl-4-(4-(methylsulfonyl)phenyl)-2-(5H)-furanone (3) or a pharmaceutically acceptable salt thereof.

43. The method of claim 37 wherein the COX-2 inhibitor is 3-(3,4-difluorophenyl)-4-(4-(methylsulfonyl)phenyl)-2-(5H)-furanone (4) or a pharmaceutically acceptable salt thereof.

44. The method of claim 37 wherein the COX-2 inhibitor is 5,5-dimethyl-4-(4-(methylsulfonyl)phenyl)-3-(3-fluorophenyl)-5H-furan-2-one (5) or a pharmaceutically acceptable salt thereof.

45. The method of claim 15 further comprising the administration of a therapeutically effective amount of at least one additional active agent selected from an HMG-CoA synthase inhibitor, a squalene epoidase inhibitor, a squalene synthetase inhibitor, an ACAT inhibitor, probucol, niacin, a fibrate, a cholesterol absorption inhibitor, a bile acid sequestrant, an LDL receptor inducer, a platelet aggregation inhibitor, vitamin $B_6$ and the pharmaceutically acceptable salts thereof, vitamin $B_{12}$, a beta-blocker, folic acid or a pharmaceutically acceptable salt or ester thereof, vitamin C, vitamin E and beta carotene.

46. A pharmaceutical composition comprising a therapeutically effective amount of an HMG-CoA reductase inhibitor, a therapeutically effective amount of a cyclooxygenase-2 inhibitor, and a pharmaceutically acceptable carrier.

47. The composition of claim 46 wherein the HMG-CoA reductase inhibitor is selected from lovastatin, simvastatin, pravastatin, fluvastatin, atorvastatin, cerivastatin and the pharmaceutically acceptable salt, ester and lactone forms thereof.

48. The composition of claim 47 wherein the HMG-CoA reductase inhibitor is selected from lovastatin and simvastatin.

49. The composition of claim 48 wherein the HMG-CoA reductase inhibitor is simvastatin.

50. The composition of claim 46 wherein the COX-2 inhibitor is selected from:
5,5-dimethyl-4-(4-(methylsulfonyl)phenyl)-3-(2-propoxy)-5H-furan-2-one (12);
5-chloro-3-(4-(methylsulfonyl)phenyl)-2-(2-methyl-5-pyridinyl)pyridine (13);
2-(3,5-difluorophenyl)-3-(4-(methylsulfonyl)phenyl)-2-cyclopenten-1-one (14);
5(S)-5-ethyl-5-methyl-4-(4-(methylsulfonyl)phenyl)-3-(2-propoxy)-5H-furan-2-one (15);
5-ethyl-5-methyl-4-(4-(methylsulfonyl)phenyl)-3-(3,4-difluorophenyl)-5H-furan-2-one (16);
3-((2-thiazolyl)methoxy)-4-(4-(methylsulfonyl)phenyl)-5,5-dimethyl-5H-furan-2-one (17);
3-propyloxy-4-(4-(methylsulfonyl)phenyl)-5,5-dimethyl-5H-furan-2-one (18);
3-( 1-cyclopropylethoxy)-5,5-dimethyl-4-(4-methylsulfonyl)phenyl)-5H-furan-2-one (19);
sodium 2-(4-chlorophenyl)-3-(4-(methylsulfonyl)phenyl)-4-oxo-2-pentenoate (20);
3-(cyclopropylmethoxy)-5,5dimethyl-4-(4-(methylsulfonyl)phenyl)-5H-furan-2-one (21);
3-(cyclopropylmethoxy)-5,5dimethyl-4-(4-(methylsulfonyl)phenyl)-2,5-dihydrofuran-2-ol (22);
3-isopropoxy-5,5-dimethyl-4-(4-(methylsulfonyl)phenyl)-2,5-dihydrofuran-2-ol (23);
5,5-Dimethyl-3-(3-fluorophenyl)-2-hydroxy-4-(4-(methylsulfonyl)phenyl)-2,5-dihydrofuran (24);
5-Chloro-3-(4-(methylsulfonyl)phenyl)-2-(3-pyridinyl)pyridine (25);
3-phenyl-4-(4-(methylsulfonyl)phenyl)-2-(5H)-furanone (3);

3-(3,4-difluorophenyl)4-(4-(methylsulfonyl)phenyl)-2-(5H)-furanone (4);
5,5-dimethyl-4-(4-(methylsulfonyl)phenyl)-3-(3-fluorophenyl)-5H-furan-2-one (5);
and the pharmaceutically acceptable salts thereof.

51. A process for preparing the pharmaceutical composition of claim 46 comprising combining the HMG-CoA reductase inhibitor with the cyclooxygenase-2 inhibitor and the pharmaceutically acceptable carrier.

52. A pharmaceutical composition made by combining a therapeutically effective amount of an HMG-CoA reductase inhibitor, a therapeutically effective amount of a cyclooxygenase-2 inhibitor, and a pharmaceutically acceptable carrier.

53. A pharmaceutical composition comprising a prophylactically effective amount of an HMG-CoA reductase inhibitor, a prophylactically effective amount of a cyclooxygenase-2 inhibitor, and a pharmaceutically acceptable carrier.

54. A method for inhibiting HMG-CoA reductase and cyclooxygenase-2 comprising the administration of an effective inhibitory amount of an HMG-CoA reductase inhibitor in combination with an effective inhibitory amount of a cyclooxygenase-2 inhibitor to a patient in need of such treatment.

* * * * *

UNITED STATES PATENT AND TRADEMARK OFFICE
CERTIFICATE OF CORRECTION

PATENT NO. : 6,245,797 B1
DATED : June 12, 2001
INVENTOR(S) : Melvin Winokur

It is certified that error appears in the above-identified patent and that said Letters Patent is hereby corrected as shown below:

Column 30,
Line 13, the poriton of the chemical name reading "3-(1-yclopropylethoxy)" should read -- 3-(1-cyclopropylethoxy) --.

Column 34,
Line 13, the word "epoidase" should read -- epoxidase --.

Signed and Sealed this

Eighth Day of June, 2004

JON W. DUDAS
*Acting Director of the United States Patent and Trademark Office*